United States Patent [19]

Frank

[11] Patent Number: 4,877,911
[45] Date of Patent: * Oct. 31, 1989

[54] PROCESS FOR PREPARING POLYALKYL TETRAHYDRONAPHTHALENES

[75] Inventor: Walter C. Frank, Holland, Pa.

[73] Assignee: Union Camp Corporation, Wayne, N.J.

[*] Notice: The portion of the term of this patent subsequent to Oct. 31, 2006 has been disclaimed.

[21] Appl. No.: 303,422

[22] Filed: Jan. 27, 1989

[51] Int. Cl.$^4$ .................. C07C 12/00; C07C 12/64; C07C 2/64

[52] U.S. Cl. .................................. 585/411; 585/410; 585/452; 585/459

[58] Field of Search ................ 585/410, 411, 452, 459

[56] References Cited

U.S. PATENT DOCUMENTS

| | | | |
|---|---|---|---|
| 3,246,044 | 6/1963 | Wood et al. | 260/668 |
| 3,379,785 | 11/1965 | Kahn | 260/668 |
| 3,856,875 | 12/1973 | Wood et al. | 260/668 F |
| 3,992,432 | 2/1975 | Napier et al. | 260/465.1 |
| 4,284,818 | 3/1979 | Sato et al. | 568/323 |
| 4,551,573 | 10/1984 | Cobb | 585/459 |
| 4,767,882 | 8/1986 | Suzukamo et al. | 560/100 |

FOREIGN PATENT DOCUMENTS

| | | |
|---|---|---|
| 2601670 | 2/1988 | France . |
| 57-40420 | 3/1982 | Japan . |
| 388527 | 3/1975 | U.S.S.R. . |

OTHER PUBLICATIONS

Boone et al., "The Acid-Catalyzed Alkylation and Cyclialkylation of the Cymenes with Isobutylene and Related Olefins", *J. Org. Chem.*, vol. 36, No. 15, pp. 2042-2048 (1971).

Coscia et al., "The Synthesis of 2,2-Ditolylpropane from αp-dimethylstyrene", *J. Org. Chem.*, vol. 26, pp. 1398-1401 (1961).

Kondo et al., "Sulfonium Salts as Liquid-Liquid Phase-Transfer Catalysts", *Synthesis*, pp. 403-404 (1988).

Kennedy, *Carbocationic Polymerization*, p. 221 (Wiley-Interscience Publishers, (1982).

*Primary Examiner*—William R. Dixon, Jr.
*Assistant Examiner*—J. Saba
*Attorney, Agent, or Firm*—Edward J. Sites

[57] ABSTRACT

A process for the production of polyalkyl tetrahydronaphthalenes is disclosed wherein a cyclialkylation reaction between an olefinic compound of the general Formula

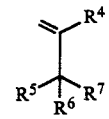

wherein $R^5$, $R^6$ and $R^7$ are independently defined and each is a substituent which does not interfere with a Friedel-Crafts type alkylation reaction, and a substituted benzene compound is carried out in the presence of an alkyl halide, a Lewis acid and a phase transfer agent. The subject process, which may be practiced in an unhalogenated hydrocarbon solvent, produces the desired compounds in a surprisingly high yield, with a surprisingly high selectivity to the desired product, and at a relatively high rate of reaction, using safer solvents and better, more convenient, or less expensive process methodology than many processes known heretofore.

38 Claims, No Drawings

PROCESS FOR PREPARING POLYALKYL TETRAHYDRONAPHTHALENES

BACKGROUND OF THE INVENTION

The present invention relates to an improved process for the production of polyalkyl tetrahydronaphthalenes, particularly 1,1,3,4,4,6-hexamethyl-1,2,3,4-tetrahydronaphthalene, the latter compound referred to herein as "HMT".

HMT and other alkyl-substituted tetrahydronaphthalenes are of significant importance to the perfumery as well as other industries. By conventional acylation processes, HMT, for example, can be converted to 7-acetyl-1,1,3,4,4,6-hexamethyl-1,2,3,4-tetrahydronaphthalene, a well known musk perfume. Because of their clean musk fragrance and ability to retain that fragrance over long periods of time, these HMT derivatives are of great commercial value as synthetic musk perfume substitutes for the expensive, natural musk perfumes of the macrocyclic ketone series. Consequently, various synthetic methods have been proposed for the production of HMT, as well as other related intermediates of HMT useful in the perfumery or other industries.

For example, Wood et al., U.S. Pat. No. 3,856,875 entitled "Process for Producing 1,1,3,4,4,6-Hexamethyl-1,2,3,4-Tetrahydronapthalene [sic] (HMT)," discusses a process for the preparation of HMT wherein an equivalent or excess amount of para-cymene is reacted with a substantially equal molar solution of neohexene (3,3-dimethyl-1-butene) and a tertiary alkyl halide in the presence of an effective amount of an anhydrous aluminum halide catalyst suspended in a reaction-compatible solvent. Although any tertiary alkyl halide can be employed in the disclosed process, tertiary butyl chloride, tertiary amyl chloride and 2,5-dichloro-2,5-dimethylhexane are noted as preferred. The process is described as having a solvent dependency, with the satisfactory solvents being ethylene dichloride, chloroform, methylene dichloride, 1,1,2,2-tetrachloroethane, 1,2-dichloroethylene, 1,2,3-trichloropropane, 1,1,2-trichloroethane, monochlorobenzene, fluorobenzene, ortho-dichlorobenzene, and para-xylene. Numerous solvents are stated to be unsatisfactory for use in the disclosed process, such solvents including nitromethane, benzene, nitrobenzene, para-cymene, n-hexane, 1,2,2-trichloroethylene, carbon tetrachloride, 1,1,1-trichloroethane, carbon disulfide, 1,1,2,2,2-pentachloroethane, 1,2-dichloropropane, 1,1-dichloroethylene, and 1,1-dichloroethane. These unsatisfactory solvents are said to yield substantially poorer results.

Wood, U.S. Pat. No. 3,246,044 entitled "Process for Making 1,1,3,4,4,6-Hexamethyl-1,2,3,4-Tetrahydronaphthalene," discloses a process for preparing HMT which includes reacting an alpha, para-dimethylstyrene derivative such as dimethyl-para-tolyl-carbinyl halide, and neohexene in the presence of a catalyst such as aluminum chloride, aluminum bromide and ferric chloride, or other Friedel-Crafts catalysts, at low temperatures. Suitable solvents are listed as ethylene dichloride or carbon tetrachloride, or other inert chlorinated hydrocarbon solvents. It is noted that other solvents such as nitrobenzene and nitromethane, may be used, but the yield of desired product is indicated as generally being lower when such solvents are employed.

Sato et al., U.S. Pat. No. 4,284,818 entitled "Process for Preparing Hexamethyltetrahydronaphthalenes," describes a process for producing HMT comprising reacting para-cymeme with a 2,3-dimethylbutene using a catalytic amount of anhydrous aluminum halide in the presence of a secondary alkyl halide, tertiary alkyl halide, propargyl halide or allyl halide. It is noted that both the 2,3-dimethyl-1-butene and 2,3-dimethyl-2-butene can be employed as the 2,3-dimethylbutene reagent, however, 2,3-dimethyl-1-butene was said to yield better results. The reaction is generally carried out using a solvent, such solvents including aliphatic hydrocarbons, halogenated aromatic hydrocarbons, and halogenated aliphatic hydrocarbons.

Cobb, U.S. Pat. No. 4,551,573 entitled "Alkylation of Aromatic Compounds," discloses a process for the alkylation of aromatic compounds with olefinic compounds in the presence of a catalyst consisting essentially of aluminum halide and elemental iodine. Examples of aromatic compounds described as suitable for use in the process include para-cymene, and olefinic compounds discussed include 2,3-dimethyl-2-butene, isobutylene and neohexene. A mixture of olefinic compounds can also be employed, in which case it is noted that one of the olefins may function as a sacrificial agent. The products of the alkylation reaction described include indanes and HMT-type compounds.

Japanese Patent Publication SHO 57-40420 discusses a method of making HMT characterized by reacting para-cymene and neohexene in the presence of anhydrous aluminum halide as catalyst. Suitable anhydrous aluminum halides are said to include aluminum chloride. The reaction is generally carried in a solvent, however, it is noted that it is possible to conduct the reaction without any additional solvent using excess para-cymene. Examples of suitable solvents are methylene chloride, ethylene chloride, chloroform and other inactive fatty hydrocarbon halides. Other solvents such as aromatic hydrocarbon halides, fatty hydrocarbons, aromatic hydrocarbons, etc., can be used, but it is noted that the use of such solvents generally lowers the yield of the desired end product.

Kahn, U.S. Pat. No. 3,379,785 entitled "Process for Preparing Polyalkyltetrahydronaphthalenes," relates to a process for preparing polyalkyl tetrahydronaphthalenes, and more specifically, a process for preparing HMT. The process involves the reaction of a substituted styrene and a 2,3-dimethylbutene, said reaction being carried out at elevated temperatures and in the presence of a cation exchange resin. The 2,3-dimethylbutene reactant employed is disclosed as comprising either 2,3-dimethyl-1-butene, 2,3-dimethyl-2-butene, or mixtures thereof. The preferably employed solvent comprises an aromatic hydrocarbon, such as, for example, benzene, toluene, ethylbenzene, or a xylene.

Suzukamo et al., U.S. Pat. No. 4,767,882 entitled "Tetrahydronaphthalene Derivatives and Their Production," discloses a process for preparing a tetrahydronaphthalene derivative in an optically active state which comprises reacting a benzene compound and a pyrocine compound in the presence of a Lewis acid, or, alternatively, reacting the benzene with the pyrocine compound in the presence of an acid catalyst followed by treatment of the resultant product with the Lewis acid.

These prior art processes suffer from various drawbacks, including low conversion of reactants, poor selectivity to the desired products, sluggish reaction rates, unacceptably low temperature requirements, unsafe solvent systems, or oxygen sensitivity. New and/or better processes are needed. The present invention is directed to this important end.

SUMMARY OF THE INVENTION

The present invention provides a process for the production of polyalkyl tetrahydronaphthalenes wherein a cyclialkylation reaction between an olefinic compound of the general Formula

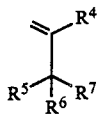

and a substituted benzene compound is carried out in the presence of an alkyl halide, a Lewis acid and a phase transfer agent. The subject process, which may be practiced in an unhalogenated hydrocarbon solvent, produces the desired compounds in a surprisingly high yield, with a surprisingly high selectivity to the desired product, and at a relatively high rate of reaction, using safer solvents and better, more convenient, or less expensive process methodology than many processes known heretofore.

Specifically, the present invention pertains to a process for producing polyalkyl tetrahydronaphthalenes, such as those represented by the Formulas

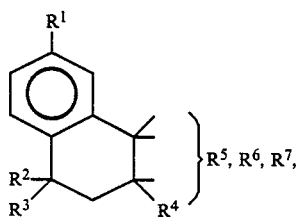 [I]

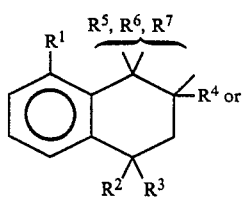 [II]

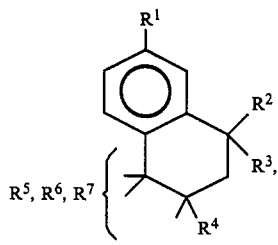 [III]

comprising contacting a partially substituted benzene compound, wherein said benzene compound is substituted with two or more substituents that do not substantially interfere with a Friedel-Crafts-type alkylation reaction said substituents including at least one secondary alkyl group having only one alpha-hydrogen, and wherein said benzene compound is unsubstituted in at least one position adjacent to said secondary alkyl group, such as those compounds of the Formulas

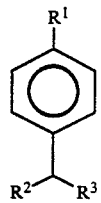 [IV]

or

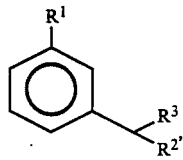 [V]

with an olefinic compound of the formula

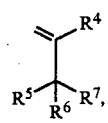 [VI]

in the presence of an alkyl halide, a Lewis acid, and a phase transfer agent. In the above Formulas, $R^1$, $R^2$, $R^3$, $R^4$, $R^5$, $R^6$ and $R^7$ are, independently, substituents that do no substantially interfere with a Friedel-Crafts-type alkylation reaction, provided that $R^1$, $R^2$, $R^3$, $R^5$, $R^6$ and $R^7$ are each other than H.

Using the foregoing process, one is able to produce a variety of alkyl-substituted tetrahydronaphthalene compounds for use as chemical intermediates and/or chemical products, particularly intermediates such as HMT, which is a compound of extreme importance to the fragrance industry.

DETAILED DESCRIPTION OF THE INVENTION

As noted above, the present invention pertains to a novel and particularly useful process for the production of polyalkyl tetrahydronaphthalenes, including, but not limited to, those of Formulas I, II or III:

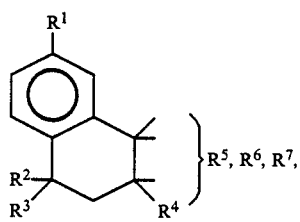 [I]

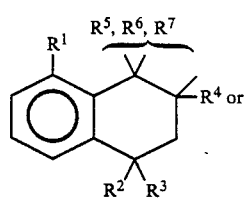 [II]

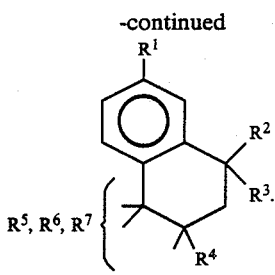

In the above Formulas, $R^1$, $R^2$, $R^3$, $R^4$, $R^5$, $R^6$, and $R^7$ are defined, independently, as substituents that do not substantially interfere with a Friedel-Crafts-type alkylation reaction, provided that $R^1$, $R^2$, $R^3$, $R^5$, $R^6$ and $R^7$ are each other than H. The bracket notation as employed in Formulas I, II and III signifies that each of substituents $R^5$, $R^6$ and $R^7$ can be present at any one of the attachment positions contained within the brackets, but not at more than one of these positions. In other words, the three attachment positions within the brackets are satisfied with an R substituent, one attachment position being satisfied with an $R^5$ substituent, another with an $R^6$ substituent, and a third with an $R^7$ substituent. Suitable $R^1$, $R^2$, $R^3$, $R^4$, $R^5$, $R^6$, and $R^7$ substituents will be readily apparent to those skilled in the art of Friedel-Crafts-type alkylation reactions. Such alkylation reactions and non-interfering substituents are discussed, for example, in George A. Olah, *Friedel-Crafts and Related Reactions*, Vols. 1 and 2 (Interscience Publishers, John Wiley and Sons, 1964) (hereinafter referred to as "*Friedel-Crafts Reactions*"), as well as in other journal and textbook references. The disclosures of *Friedel-Crafts Reactions* are incorporated herein by reference. Examples of suitable substituents include those wherein $R^4$ is H, or a $C_1$–$C_{30}$ straight chain, branched or cyclical alkyl, and $R^1$, $R^2$, $R^3$, $R^5$, $R^6$ and $R^7$, independently, are a $C_1$–$C_{30}$ straight chain, branched or cyclical alkyl. The alkyl is preferably a $C_1$–$C_{20}$, more preferably a $C_1$–$C_{10}$, and most preferably a $C_1$–$C_5$, alkyl. Preferably, the alkyl is a straight chain or branched alkyl. In a generally preferred embodiment, $R^1$, $R^2$, $R^3$, $R^5$, $R^6$ and $R^7$, independently, are a $C_1$–$C_5$ straight chain or branched alkyl, and $R^4$ is H.

In a most preferred embodiment, the polyalkyl tetrahydronaphthalenes are of the Formula I. The Formula I compounds are preferably:

1,1,3,4,4,6-hexamethyl-1,2,3,4-tetrahydronaphthalene (that is, HMT, a compound of Formula I wherein $R^1$, $R^2$, $R^3$, $R^5$, $R^6$ and $R^7$ are each methyl, and $R^4$ is H);

6-ethyl-1,1,3,4,4-pentamethyl-1,2,3,4-tetrahydronaphthalene (that is, a compound of Formula I wherein $R^1$ is ethyl, and $R^2$, $R^3$, $R^5$, $R^6$ and $R^7$ are each methyl, and $R^4$ is H);

6-tertiary-butyl-1,1,3,4,4-pentamethyl-1,2,3,4-tetrahydronaphthalene (that is, a compound of Formula I wherein $R^1$ is tertiary butyl, and $R^2$, $R^3$, $R^5$, $R^6$ and $R^7$ are each methyl, and $R^4$ is H); and 6-n-propyl-1,1,3,4,4-pentamethyl-1,2,3,4-tetrahydronaphthalene (that is, a compound of Formula I wherein $R^1$ is n-propyl, and $R^2$, $R^3$, $R^5$, $R^6$ and $R^7$ are each methyl, and $R^4$ is H).

The compounds of Formulas I, II and III are produced by contacting a partially substituted benzene compound, wherein said benzene compound is substituted with one or more substituents that do not substantially interfere with a Friedel-Crafts-type alkylation reaction said substituents including at least one secondary alkyl group having only one alpha-hydrogen, and wherein said benzene compound is unsubstituted in at least one position adjacent to said secondary alkyl group, such substituted benzene compounds including, but not limited to, those of the Formulas IV or V

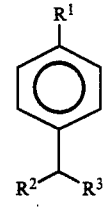

with an olefinic compound of the Formula VI

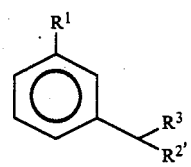

As those skilled in the art would recognize, contacting a benzene compound of Formula IV with an olefinic compound of Formula VI will yield the tetrahydronaphthalene compounds of Formula I. Alternatively, contacting a benzene compound of Formula V with an olefinic compound of Formula VI will yield the tetrahydronaphthalene compounds of Formulas II and III. As will be recognized by those skilled in the art, the Formula I, II or III compounds may isomerize under the reaction conditions to also form compounds of one or more of the other Formulas I, II or III.

In the above Formulas IV, V and VI, $R^1$, $R^2$, $R^3$, $R^4$, $R^5$, $R^6$, and $R^7$ are defined, independently, as previously described, that is, as substituents that do not substantially interfere with a Friedel-Crafts-type alkylation reaction, provided that $R^1$, $R^2$, $R^3$, $R^5$, $R^6$ and $R^7$, are each other than H. Suitable substituents are discussed in various journal and textbook references, such as *Friedel-Crafts Reactions*. Suitable substituents include those wherein $R^4$ is H, or a $C_1$–$C_{30}$ straight chain, branched or cyclical alkyl, and $R^1$, $R^2$, $R^3$, $R^5$, $R^6$ and $R^7$, independently, are a $C_1$–$C_{30}$ straight chain, branched or cyclical alkyl. The alkyl is preferably a $C_1$–$C_{20}$, more preferably a $C_1$–$C_{10}$, and most preferably a $C_1$–$C_5$, alkyl. Preferably the alkyl is a straight chain or branched alkyl.

With respect to the benzene compounds of Formulas IV and V, a generally preferred embodiment includes those compounds wherein $R^1$, $R^2$ and $R^3$, independently, are a $C_1$–$C_5$ straight chain or branched alkyl. In a most preferred embodiment, the substituted benzene compounds are of Formula IV. The Formula IV compounds are preferably isopropyl toluene (that is, paracymene, a compound of Formula IV wherein $R^1$, $R^2$ and $R^3$ are each methyl), 1-ethyl-4-isopropylbenzene (that is, a compound of Formula IV wherein $R^1$ is ethyl, and $R^2$ and $R^3$ are each methyl), 1-n-propyl-4-isopropylbenzene (that is, a compound of Formula IV wherein $R^1$ is n-propyl, and $R^2$ and $R^3$ are each methyl), and 1-tertiary-butyl-4-isopropylbenzene (that is, a compound of Formula IV wherein $R^1$ is tertiary-butyl, and $R^2$ and $R^3$ are each methyl).

In a generally preferred embodiment, the olefinic compounds of Formula VI include those compounds wherein $R^4$ is H or a $C_1$–$C_5$ straight chain or branched alkyl, and $R^5$, $R^6$ and $R^7$, independently, are a $C_1$–$C_5$ straight chain or branched alkyl. A more preferable embodiment is wherein $R^4$ is H. Of the Formula VI compounds, 3,3-dimethyl-1-butene (that is, neohexene, a compound of Formula VI wherein $R^4$ is H, and $R^5$, $R^6$ and $R^7$ are each methyl) is most preferred.

In accordance with the present invention, the compounds of Formulas IV or V are contacted with compounds of Formula VI in the presence of an alkyl halide, a Lewis acid, and a phase transfer agent.

Suitable alkyl halides include, but are not limited to secondary alkyl halides, tertiary alkyl halides, propargyl halides and allyl halides. Exemplary secondary alkyl halides include isopropyl chloride, secondary-butyl chloride, secondary-amyl chloride, cyclohexyl chloride, and homologues thereof having fluorine, bromine or iodine atoms substituted for the chlorine atom, as well as various secondary alkyl dihalides. Examples of tertiary alkyl halides include tertiary-butyl chloride, tertiary-amyl chloride, 2-methyl-2-chloropentane, 3-methyl-3-chloropentane, as well as various other tertiary alkyl dihalides such as 1,8-dichloro-para-menthane, and homologues thereof having fluorine, bromine or iodine atoms substituted for the chlorine atom. Representative propargyl halides include propargyl chloride, 1-chloro-2-butyne, 1-chloro-2-pentyne, and homologues thereof having fluorine, bromine or iodine atoms substituted for the chlorine atom, as well as various propargyl dihalides. Suitable allyl halides include allyl chloride, 1-chloro-2-butene, 1-chloro-3-methyl-2-butene, 1-chloro-2-pentene, 1-chloro-2-hexene and homologues thereof having fluorine, bromine or iodine atoms substituted for the chlorine atom, as well as various allyl dihalides. Other suitable alkyl halides will be readily apparent to those skilled in the art. Of the foregoing alkyl halides, tertiary alkyl halides, and in particular tertiary-butyl chloride, tertiary-amyl chloride, 2-methyl-2-chloropentane, 3-methyl-3-chloropentane and 1,8-dichloro-para-menthane, are preferred. A most preferred alkyl halide is the tertiary alkyl halide which is tertiary-butylchloride.

Any Lewis acid, that is, any non-protonic compounds capable of accepting an electron pair, is suitable for use in the present process. Exemplary Lewis acids include metal halides such as aluminum halides (including aluminum chloride aluminum bromide, aluminum iodide, monofluorodichloroaluminum, monobromodichloroaluminum and monoiododichloroaluminum). Alkyl metals and alkyl metal halides suitable for use as Lewis acids in the present process are disclosed, for example, in Kennedy, Joseph P., *Carbocationic Polymerization*, p. 221 (Wiley-Interscience Publishers (1982)), the disclosures of which are incorporated herein by reference. In the process of the present invention, aluminum halides are preferred. Of the aluminum halides, aluminum chloride and aluminum bromide, particularly aluminum chloride, are most preferred.

Suitable phase transfer agents include onium salts such as ammonium, phosphonium and sulfonium salts. Other phase transfer agents suitable for use in the present process will be readily apparent to those skilled in the art, once having been made aware of the present disclosure.

Examples of ammonium phase transfer agents include quaternary ammonium halides such as methyltrioctylammonium chloride, methyltrinonylammonium chloride, methyltridecylammonium chloride, hexadecyltrihexylammonium bromide, ethyltrioctylammonium bromide, didodecyldimethylammonium chloride, tetraheptylammonium iodide, dioctadecyldimethylammonium chloride, tridecylbenzylammonium chloride ditricosylmethylammonium chloride, and homologues thereof having chlorine, fluorine, bromine or iodine atoms substituted for the enumerated halide atom. Also suitable for use in the present invention as phase transfer agents are tertiary amine compounds substituted with hydrocarbons, such as trioctyl amine, which, under the conditions of the subject process may be converted to form quaternary ammonium salts.

Exemplary phosphonium phase transfer agents include quaternary phosphonium halides such as tributyldecylphosphonium iodide, triphenyldecylphosphonium iodide, tributylhexadecylphosphonium iodide, and homologues thereof having chlorine, fluorine or bromine atoms substituted for the iodine atom. In addition, trisubstituted phosphine compounds substituted with hydrocarbons, such as tri-n-butyl phosphine, may be converted to quaternary phosphonium salts under the present reaction conditions, and as such, are also suitable for use in the subject process as phase transfer agents.

Representative sulfonium phase transfer agents include ternary sulfonium halides such as lauryldimethylsulfonium iodide, lauryldiethylsulfonium iodide and tri(n-butyl)sulfonium iodide, and homologues thereof having chlorine, fluorine or bromine atoms substituted for the iodine atom. In addition, disubstituted sulfur compounds substituted with hydrocarbons may be converted to ternary sulfonium salts under the present reaction conditions, and as such, are also suitable for use in the subject process as phase transfer agents.

These and other suitable phase transfer agents are described, for example, in Napier et al., U.S. Pat. No. 3,992,432 entitled "Phase Transfer Catalysis of Heterogeneous Reactions by Quaternary Salts," and in Kondo et al., *Synthesis*, pp. 403–404 (May 1988), the disclosures of which are incorporated herein by reference.

Preferable phase transfer agents are ammonium or sulfonium salts, particularly quaternary ammonium or ternary sulfonium halides. Most preferred are quaternary ammonium halides, particularly methyltrioctylammonium chloride (referred to herein as "MTOAc"), and a mixture of methyltrioctylammonium chloride and methyltridecylammonium chloride. The latter mixture is marketed under the trademark Adogen-464 TM, by Sherex Co., located in Dublin, Ohio.

In general, the molar proportions of the reagents employed in the present process can be varied over a relatively wide range. For the best results, however, it is important to maintain a ratio of less than one mole of phase transfer agent per mole of Lewis acid. Preferably, the molar ratio is about 0.8 to 1.0, more preferably 0.5 to 1.0, phase transfer agent to Lewis acid. It should be noted that some phase transfer agents sold commercially are sold in an impure form. Such impurities generally comprise water or an alcohol species. Water and alcohol, as well as other impurities, will react adversely with the Lewis acid, thereby lowering the amount of active Lewis acid available for the process of the present invention. Accordingly, where the phase transfer agent added contains such impurities, the amount of Lewis acid should be increased to account for these impurities. In such a situation the ratio of transfer agent to Lewis acid might be about 0.3 to 1.0. Such impure agent-containing mixtures are referred to herein as mixtures in an "impure form".

It is preferable to use a mixture of olefinic compound and alkyl halide wherein these components are present in a range of about 1.0 to about 5.0 moles of olefin per mole of halide. More preferably, the olefin and alkyl halide are present in nearly equimolar amounts, that is, about 1.0 to 1.0.

Preferably, the substituted benzene compound is present in a range of about 0.5 to about 10 moles per mole of olefin. More preferably, the substituted benzene compound is present in a range of about 0.5 to about 5.0 per mole of olefin.

In a most preferred embodiment, each of the benzene compound, olefin and alkyl halide are present nearly in equimolar amounts.

The amount of Lewis acid utilized is preferably in the range of about 2% to about 10% by weight of the Lewis acid based on the combined weight of the substituted benzene, olefin and alkyl halide.

The reaction is generally carried out using a solvent, although, if desired, substituted benzene, one of the starting materials, may be employed in large excess in lieu of an additional solvent. Surprisingly, a number of different solvents may be utilized in the present invention, including unhalogenated aliphatic, unhalogenated alicyclic and unhalogenated aromatic hydrocarbon solvents. Such unhalogenated aliphatic, unhalogenated alicyclic and unhalogenated aromatic hydrocarbon solvents are particularly preferred for reasons of safety. Exemplary of these preferred solvents are the aliphatic solvents n-hexane, n-heptane and n-octane, the alicyclic solvent cyclohexane, and the aromatic solvents benzene, toluene, ethylbenzene and xylene. Particularly preferred for reasons of yield, safety and/or process engineering are the unhalogenated aliphatic and unhalogenated alicyclic hydrocarbons. Other suitable solvents are described, for example, in U.S. Pat. Nos. 4,284,818, 3,856,875 and 3,379,785, the disclosures of which are incorporated herein by reference.

The alkylation reaction of the invention can be carried out in any suitable vessel which provides efficient contacting between the Lewis acid, the phase transfer agent and the other reactants. For simplicity, a stirred batch reactor can be employed. Although stirring is recommended to provide efficient contact between reactants, it has been found that with the addition of the phase transfer agent pursuant to the present invention, the Lewis acid is able to solubilize rather quickly, thereby obviating the need for the stringent stirring requirements of many of the art processes utilized to produce HMT. The reaction vessel used should be resistant to the possibly corrosive nature of the catalyst. Glass-lined vessels are suitable for this purpose, as well as other vessel materials well-known in the art.

The reagents of the present process may be added in any order, although a preferred mode of carrying out the process is to add the solvent, the Lewis acid and the phase transfer agent first, allow sufficient time for the Lewis acid to become substantially dissolved in the solvent, and then add the remaining reagents. Generally, 15 to 30 minutes are needed for the Lewis acid to become substantially dissolved in the solvent.

Ideally, the reaction is carried out at a temperatures ranging from about $-30°$ C. to about $50°$ C., preferably at temperatures ranging from about $-10°$ C. to about $40°$ C., and most preferably at temperatures ranging from about $0°$ C. to about $30°$ C.

The pressure at which the reaction is carried out is not critical. If the reaction is carried out in a sealed vessel, autogenous pressure is acceptable, although higher or lower pressures, if desired, may be employed. The reaction can also be carried out at atmospheric pressure in an open reaction vessel, in which case the vessel is preferably equipped with a moisture trap to prevent significant exposure of Lewis acid to moisture. The reaction can take place in an oxygen atmosphere, or an inert atmosphere as in the presence of a gas such as nitrogen, argon and the like, the type of atmosphere also not being critical.

Reaction time is generally rather short and is often dictated by the kind of equipment employed. Sufficient time must be provided, however, for thorough contacting of the substituted benzene compound, the olefinic compound, the Lewis acid and the phase transfer agent. Generally the reaction proceeds to completion in about 1 to about 7 hours.

Product can be recovered by first quenching the reaction mixture in cold water or on crushed ice, preferably on ice, and then processing the mixture in the usual manner for Friedel-Crafts reactions to extract the desired alkyl-substituted tetrahydro-naphthalene compounds. Suitable extraction protocol is described, for example, in *Friedel-Crafts Reactions*. Typically, following quenching and the resultant phase separation, the organic layer is washed an additional time with water to aid in removal of the Lewis acid. One or more additional washings can be carried out with dilute alkali solution to further aid Lewis acid removal. Pure product can then be recovered by subjecting the washed reaction mixture to reduced pressure fractional distillation.

The polyalkyl tetrahydronaphthalenes prepared in accordance with the processes of the invention, as hereinbefore indicated, may, for example be acylated to obtain acylated polyalkyl tetrahydronaphthalenes having very fine, musk-like fragrances, a characteristic which renders them highly valuable for use in the perfumery industry. Such products, acylated or otherwise, may alternatively or additionally have utility in the pharmaceutical and/or agrochemical industries, either as intermediates or as end products, as generally discussed in French Patent Publication No. 2601670, and U.S. Pat. No. 4,551,573. The acylation process may be carried out using conventional methods, such as by reacting the polyalkyl tetrahydronaphthalene with an acyl halide or acid anhydride in the presence of an acid-acting catalyst. Suitable acylation methods are well known in the art and are disclosed, for example, in U.S. Pat. No. 4,284,818. Examples of acylated polyalkyl tetrahydronaphthalenes include 7-acetyl-1,1,3,4,4,6-hexamethyl-1,2,3,4-tetrahydronaphthalene, 7-acetyl-1,1,3,4,4-pentamethyl-6-ethyl-1,2,3,4-tetrahydronaphthalene, 7-acetyl-1,1,3,4,4-pentamethyl-6-n-propyl-1,2,3,4-tetrahydronaphthalene, and 7-acetyl-1,1,3,4,4-pentamethyl-6-tertiary-butyl-1,2,3,4-tetrahydronaphthalene.

The present invention is further described in the following Examples. These Examples are not to be construed as limiting the scope of the appended claims.

In each Example, the reaction flasks were equipped with a condenser, mechanical stirrer, addition funnel and thermocouple/temperature controller connected to an automatic laboratory jack. The flasks were cooled, when necessary, with a dry ice/isopropanol bath. The flask contents were continuously stirred throughout the reaction.

Results were analyzed on both polar and non-polar gas chromatography columns. All gas chromatography analyses were carried out on capillary columns using a weight percent internal standard method of analysis. Structure identifications were assigned based on GCMS fragmentation patterns compared to standards.

Examples 1 and 5 below are provided for comparative purposes only, and do not illustrate processes of the present invention. Specifically, Example 1 and 5 were carried out substantially in accordance with the procedures set forth in U.S. Pat. Nos. 4,284,818 and 3,856,875, respectively. Examples 2–4 and 6–8 are examples of processes of the present invention.

EXAMPLE 1 (Comparative Example)

Cyclohexane (19.10 g) and anhydrous aluminum chloride (1.80 g) were added to a 50 ml four-necked round bottom flask. The flask was charged with a well-stirred mixture of para-cymene (25.13 g, 98%), neohexene (7.96 g, 97%) and tertiary-butyl chloride (9.52 g, 98%), over about a three-hour period. During the addition process, the temperature of the flask was maintained at about 17°-20° C. with the aid of the temperature controller, automatic laboratory jack, and dry ice/isopropanol bath. During the first two hours of addition, a large amount of orange solids appeared on the sides of the flask. During the last hour of addition, these solids went back into solution. After addition was completed, the reaction was quenched with ice water (20 ml), and the resultant product washed with, in order, 5% aqueous HCl, 10% aqueous $Na_2CO_3$, and water. All aqueous layers were individually extracted with ether, the ether layers combined with the initial organic phase and evaporated to yield a crude product (30.75 g) containing 24.55 weight % of 1,1,3,4,4,6-hexamethyl-1,2,3,4-tetrahydronaphthalene (HMT) (7.55 g, 38.1% molar yield based on neohexene charged).

This example was carried out substantially in accordance with the procedure set forth in Sato et al., U.S. Pat. No. 4,284,818 entitled "Process for Preparing Hexamethyltetrahydronaphthalenes," example #8, with the exception that the 2,3-dimethyl-1-butene has been replaced with neohexene.

This example shows that neohexene cannot be substituted for 2,3-dimethyl-1-butene when the reaction is carried out as described in Sato et al. without a loss in product yield. This is in direct agreement with the findings of Wood and Heilweil, U.S. Pat. No. 3,856,875 entitled "Process for Producing 1,1,3,4,4,6-Hexamethyl-1,2,3,4-Tetrahydronaphthalene [sic] (HMT), " which lists hydrocarbon solvent, such as hexane, as unsatisfactory.

EXAMPLE 2

A 50 ml three-necked round bottom flask was charged with cyclohexane (9.55 g), anhydrous aluminum chloride (0.912 g), methyltrioctylammonium chloride (1.37 g, 97% pure) and stirred for about 5 minutes. To the flask was then added a mixture of neohexene (3.82 g, 97% pure), tertiary-butyl chloride (4.81 g, 99% pure), and para-cymene (12.57 g, 96% pure). During the addition process, the temperature of the flask was maintained at about 20° C. Over a period of about 3 hours, the resultant product was then treated as in Example 1, to yield a crude product (14.96 g) containing 30.8 weight % HMT (48.5% molar yield based on neohexane charged).

This example was carried out within the procedure of Example 1 of this disclosure, with the exception that a phase transfer agent, methyltrioctylammonium chloride, was added in accordance with the teachings of this invention. This resulted in an approximate yield increase of 27% over Example 1.

EXAMPLE 3

A 50 ml three-necked round bottom flask was charged with cyclohexane (9.55 g), tertiary-butyl chloride (4.81 g) and para-cymene (12.57 g) and cooled to 0° C. Next, anhydrous aluminum chloride (0.914 g) and methyltrioctylammonium chloride (1.37 g) were added to the flask. Neohexene (3.82 g, 97% pure) was then added over a period of about three hours, with the temperature of the flask being maintained at about 0° C., then treated as described in Example 1 to yield a crude product (15.26 g) containing 42.3 weight % HMT (67.8% molar yield based on neohexene charged).

This example is an example of the present invention demonstrating an alternative mode of reagent addition.

EXAMPLE 4

A 100 ml four-necked round bottom flask was charged with Adogen-464 ™ (1.515 g), cyclohexane (19.10 g) and the flask was cooled to about 16° C. The anhydrous aluminum chloride (1.43 g) was then added and the mixture stirred for about 0.5 hours while maintaining the flask at about 16° C. Next, a mixture of para-cymene (25.14 g) and tertiary-butyl chloride (8.40 g) was added to the flask. Immediately thereafter, neohexene addition was started (via syringe pump), while the flask temperature was adjusted to and maintained at about 0° C. A total of 7.64 g neohexene (97% pure) was added over a period of about 1.5 hours. After stirring an additional 0.5 hours, the reaction was then quenched with water (10 ml) and the resultant product treated as previously described, to yield a crude product (30.00 g) containing 36.22 weight % HMT (57.1% molar yield based on neohexene charged).

This example is an example of the present invention, demonstrating the use of the commercially available phase transfer agent Adogen 464 ™.

EXAMPLE 5 (Comparative Example)

A 100 ml three-necked round bottom flask was charged with 1,2 dichloroethane (10.10 g) and anhydrous aluminum chloride (0.962 g). The flask was cooled to about −8° C. An addition funnel was charged with paracymene (31.67 g), tertiary-butyl chloride (10.61 g) and neohexene (8.84 g, 97% pure), and the funnel reagents were added over a period of about 2 hours while maintaining the temperature of the flask at about −6° to −8° C. After 3 hours of additional stirring while maintaining that same temperature, the reaction was quenched with ice water (20 ml), and treated as described in Example 1 yield a crude product (37.46 g) containing 35.63 weight % HMT (60.6% molar yield based on neohexene charged).

This example was carried out substantially in accordance with the procedure set forth in Wood and Heilweil.

EXAMPLE 6

A 50 ml three-necked round bottom flask was charged with anhydrous aluminum chloride (0.50 g), Adogen-464 TM (0.83 g) and 1,2-dichloroethane (7.51 g). The mixture was cooled to about −8° C. An addition funnel was charged with para-cymene (15.20 g), tertiary-butyl chloride (5.23 g) and neohexene, (4.20 g, 97% pure), and the funnel reagents added over a period of about 1.75 hours while maintaining a temperature of about −6° to −8° C. This temperature was maintained for an additional three hours while stirring was continued. The reaction was then quenched with ice water (10 ml) and treated as described in Example 1 to yield a crude product (17.84 g) containing 34.3 weight % HMT (58.5% molar yield based on neohexene charged).

This example was carried out in the same fashion as Example 5, with the exception that the phase transfer agent Adogen 464 TM was added. This shows that under satisfactory solvent conditions as described in Wood and Heilweil, no yield advantage is noted upon addition of a phase transfer agent.

EXAMPLE 7

A 50 ml three-necked round bottom flask was charged with cyclohexane (9.55 g), para-cymene (12.57 g), and 1,8-dichloro-para-menthane (5.43 g). The reaction was cooled to about 0° C. and anhydrous aluminum chloride (0.913 g) and methyltrioctylammonium chloride (1.368 g) were quickly added. Immediately neohexene (3.48 g, 97% purity) was added via syringe pump over a period of about 2 hours at about 0° C. After about 4.5 hours additional stirring while maintaining that same temperature, the reaction was quenched with water (10 ml) and treated as described in Example 1 to yield a crude product (18.15 g) containing 25.86 weight % HMT (54.1% molar yield based on neohexene charged).

This example describes the use of the dihalide 1,8-dichloro-para-menthane in accordance with the teachings of this invention.

EXAMPLE 8

A 100 ml four-necked round bottom flask was charged with trioctylamine (1.23 g), cyclohexane (19.10 g), and anhydrous aluminum chloride (1.43 g). The flask was cooled to about 20° C. and stirred for about 0.5 hours. Next, para-cymene (25.14 g) was added to the flask. Following the cymene addition, tertiary-butyl chloride (7.70 g) and neohexene (7.09 g, 97% pure) were added independently at 20° C. over a period of about 1 hour and 2 hours, respectively. Addition of neohexene was such that the initial rate was faster than the final rate, by a factor of about 2. The tertiary-butyl chloride addition rate was linear. One hour after the neohexene addition was complete, the reaction was quenched with water (20 ml) and worked up as described in Example 1 to yield a crude product (29.15 g) containing 28.0 weight % HMT (46.2 mole % yield based on neohexene charged).

Example 8 describes the use of trioctylamine as the phase transfer agent in accordance with the teaching of this invention.

Various modifications of the invention, in addition to those shown and described herein, will be apparent to those skilled in the art from the foregoing description. Such modifications are also intended to fall within the scope of the appended claims.

What is claimed is:

1. A process for producing a polyalkyl tetrahydronaphthalene compound comprising contacting a partially substituted benzene compound, wherein said benzene compound is substituted with two or more substituents that do not substantially interfere with a Friedel-Crafts-type alkylation reaction said substituents including at least one secondary alkyl group having only one alpha-hydrogen, and wherein said benzene compound is unsubstituted in at least one position adjacent to said secondary alkyl group, with an olefinic compound of the Formula

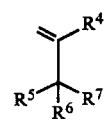

[VI]

wherein $R^4$, $R^5$, $R^6$, and $R^7$, independently, are substituents that do not substantially interfere with a Friedel-Crafts-type alkylation reaction, provided that $R^5$, $R^6$ and $R^7$ are each other than H, in the presence of
 an alkyl halide,
 a Lewis acid, and
 a phase transfer agent.

2. A process for producing a polyalkyl tetrahydronaphthalene compound of the Formulas

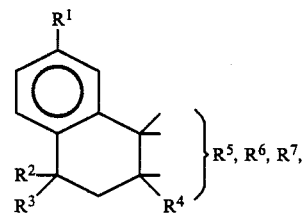

[I]

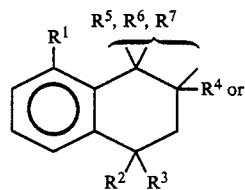

[II]

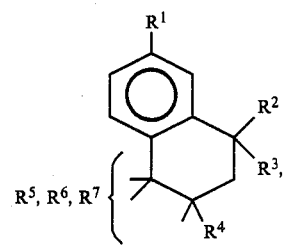

[III]

comprising contacting a partially substituted benzene compound of the Formulas

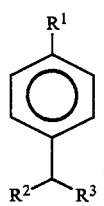

[IV]

-continued
or

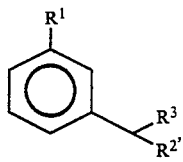

with an olefinic compound of the Formula

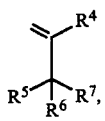

in the presence of
  an alkyl halide,
  a Lewis acid, and
  a phase transfer agent,
wherein
  $R^1$, $R^2$, $R^3$, $R^4$, $R^5$, $R^6$, and $R^7$, independently, are substituents that do not substantially interfere with a Friedel-Crafts-type alkylation reaction, provided that $R^1$, $R^2$, $R^3$, $R^5$, $R^6$ and $R^7$ are each other than H.

3. A process of claim 2 wherein
  $R^4$ is H, or a $C_1$-$C_{30}$ straight chain, branched or cyclical alkyl; and
  $R^1$, $R^2$, $R^3$, $R^5$, $R^6$, and $R^7$, independently, are a $C_1$-$C_{30}$ straight chain, branched or cyclical alkyl.

4. A process of claim 3 wherein said alkyl is a $C_1$-$C_5$ alkyl.

5. A process of claim 3 wherein said alkyl is a straight chain or branched alkyl.

6. A process of claim 3 wherein said polyalkyl tetrahydronaphthalene compound is of the Formula.

7. A process of claim 6 wherein
  $R^1$, $R^2$, $R^3$, $R^5$, $R^6$ and $R^7$, independently, are a $C_1$-$C_5$ straight chain or branched alkyl; and
  $R^4$ is H.

8. A process of claim 7 wherein
  $R^1$, $R^2$, $R^3$, $R^5$, $R^6$ and $R^7$ are each methyl.

9. A process of claim 7 wherein
  $R^1$ is ethyl; and
  $R^2$, $R^3$, $R^5$, $R^6$ and $R^7$ are each methyl.

10. A process of claim 7 wherein
  $R^1$ is n-propyl; and
  $R^2$, $R^3$, $R^5$, $R^6$ and $R^7$ are each methyl.

11. A process of claim 7 wherein
  $R^1$ is tertiary butyl; and
  $R^2$, $R^3$, $R^5$, $R^6$ and $R^7$ are each methyl.

12. A process of claim 3 wherein said partially substituted benzene compound is of the Formula [IV].

13. A process of claim 12 wherein
  $R^1$, $R^2$ and $R^3$, independently, are a $C_1$-$C_5$ straight chain or branched alkyl.

14. A process of claim 13 wherein
  $R^1$, $R^2$ and $R^3$ are each methyl.

15. A process of claim 13 wherein
  $R^1$ is ethyl; and
  $R^2$ and $R^3$ are each methyl.

16. A process of claim 13 wherein
  $R^1$ is n-propyl; and
  $R^2$ and $R^3$ are each methyl.

17. A process of claim 13 wherein
  $R^1$ is tertiary-butyl; and
  $R^2$ and $R^3$ are each methyl.

18. A process of claim 3 wherein
  $R^4$ is H or a $C_1$-$C_5$ straight chain or branched alkyl; and
  $R^5$, $R^6$ and $R^7$, independently, are a $C_1$-$C_5$ straight chain or branched alkyl.

19. A process of claim 18 wherein
  $R^4$ is H.

20. A process of claim 18 wherein
  $R^4$ is H; and
  $R^5$, $R^6$ and $R^7$ are each methyl.

21. A process of claim 2 wherein said alkyl halide is selected from the group consisting of secondary alkyl halides, tertiary alkyl halides, propargyl halides and allyl halides.

22. A process of claim 21 wherein said alkyl halide is a tertiary alkyl halide selected from the group consisting of tertiary-butyl chloride, tertiary-amyl chloride, 2-methyl-2-chloropentane, 3-methyl-3-chloropentane, 1,8-dichloro-para-menthane and homologues thereof having fluorine, bromine or iodine atoms substituted for the chlorine atom.

23. A process of claim 22 wherein said tertiary alkyl halide is tertiary-butyl chloride.

24. A process of claim 2 wherein said Lewis acid is selected from the group consisting of metal halides, alkyl metal halides and alkyl metals.

25. A process of claim 24 wherein said Lewis acid is metal halide which is an aluminum halide.

26. A process of claim 25 wherein said aluminum halide is aluminum chloride.

27. A process of claim 2 wherein said phase transfer agent is selected from the group consisting of ammonium, phsophonium and sulfonium salts.

28. A process of claim 27 wherein said ammonium salt is a quaternary ammonium halide.

29. A process of claim 28 wherein said quaternary ammonium halide is methyltrioctylammonium chloride.

30. A process of claim 28 wherein said quaternary ammonium halide is a mixture of methyltridecylammonium chloride and methyltridecylammonium chloride.

31. A process of claim 2 wherein said phase transfer agent is a tertiary amine compound substituted with hydrocarbons.

32. A process of claim 31 wherein said tertiary amine compound substituted with hydrocarbons is trioctyl amine.

33. A process of claim 2 wherein said phase transfer agent and said Lewis acid are present in a molar ratio of less than 1 to 1, phase transfer agent to Lewis acid.

34. A process of claim 33 wherein said phase transfer agent and said Lewis acid are present in a molar ratio of about 0.5 to 1.0.

35. A process of claim 33 wherein said phase transfer agent is in an impure form and said phase transfer agent and said Lewis acid are present in a molar ratio of about 0.3 to 1.

36. A process of claim 2 further comprising a solvent.

37. A process of claim 36 wherein said solvent is selected from the group consisting of unhalogenated aliphatic, unhalogenated alicyclic and unhalogenated aromatic hydrocarbon solvents.

38. A process of claim 37 wherein said unhalogenated alicyclic solvent is cyclohexane.

* * * * *